US011259687B2

(12) United States Patent
Algawi et al.

(10) Patent No.: US 11,259,687 B2
(45) Date of Patent: Mar. 1, 2022

(54) MEDICAL INSTRUMENT CALIBRATION

(71) Applicant: BIOSENSE WEBSTER (ISRAEL) LTD., Yokneam (IL)

(72) Inventors: Yehuda Algawi, Binyamina (IL); Assaf Govari, Haifa (IL); Ilya Sitnitsky, Nahariya (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 51 days.

(21) Appl. No.: 16/797,634

(22) Filed: Feb. 21, 2020

(65) Prior Publication Data
US 2020/0315427 A1  Oct. 8, 2020

Related U.S. Application Data

(60) Provisional application No. 62/829,517, filed on Apr. 4, 2019.

(51) Int. Cl.
| | |
|---|---|
| *B25B 11/00* | (2006.01) |
| *A61B 1/00* | (2006.01) |
| *A61B 1/015* | (2006.01) |
| *A61B 1/05* | (2006.01) |
| *A61B 1/06* | (2006.01) |
| *B25B 11/02* | (2006.01) |

(52) U.S. Cl.
CPC ........ *A61B 1/00057* (2013.01); *A61B 1/0011* (2013.01); *A61B 1/015* (2013.01); *A61B 1/051* (2013.01); *A61B 1/0676* (2013.01); *A61B 1/0684* (2013.01); *B25B 11/02* (2013.01)

(58) Field of Classification Search
CPC ........... B25B 11/00; B25B 11/02; B23Q 5/00; B23Q 3/06; A61B 1/00057; A61B 1/011; A61B 1/015
See application file for complete search history.

(56) References Cited

U.S. PATENT DOCUMENTS 3,872,567 A * 3/1975 Cea .................. H01R 43/01
29/721
6,124,548 A * 9/2000 Suzuki ............. H01B 13/01209
140/93 R
(Continued)

FOREIGN PATENT DOCUMENTS

EP      1111386 A2   6/2001
WO   WO 2009/140757   11/2009
(Continued)

OTHER PUBLICATIONS

European Search Report dated Aug. 10, 2020 from corresponding European Patent Application No. 20167943.8.

*Primary Examiner* — Lee D Wilson

(57) ABSTRACT

In one embodiment, a calibration apparatus includes a jig body, a camera, an elongated strip which is deflectable and resilient, a lower groove which is disposed in the jig body, and is configured to receive and grasp the camera therein, an upper groove, which is disposed in the jig body above the lower groove, and is configured to receive and grasp the elongated strip therein so as to position the elongated strip above, and in a fixed relation to, the camera, the upper groove being wider than the lower groove, and an alignment element, which is disposed in the jig body, and is configured to align an end of the camera with an end of the elongated strip.

9 Claims, 5 Drawing Sheets

(56) References Cited

U.S. PATENT DOCUMENTS

| | | | |
|---|---|---|---|
| 9,188,973 | B2 | 11/2015 | Tenney et al. |
| 9,838,576 | B2 | 12/2017 | Haraguchi et al. |
| 10,092,215 | B2 | 10/2018 | Salamini et al. |
| 2013/0281821 | A1 | 10/2013 | Liu et al. |
| 2017/0087873 | A1* | 3/2017 | Freybler ............ B23K 26/0673 |
| 2017/0107469 | A1 | 4/2017 | Costa et al. |
| 2017/0360309 | A1 | 12/2017 | Moore et al. |
| 2020/0315427 | A1* | 10/2020 | Algawi .............. A61B 1/00064 |

FOREIGN PATENT DOCUMENTS

| | | |
|---|---|---|
| WO | WO2011/010632 | 1/2011 |
| WO | WO2012/096102 | 7/2012 |

* cited by examiner

MEDICAL INSTRUMENT CALIBRATION

RELATED APPLICATION INFORMATION

The present application claims benefit of U.S. Provisional Patent Application No. 62/829,517 of Algawi, et al., filed on Apr. 4, 2019.

FIELD OF THE INVENTION

The present invention relates to medical instruments, and in particular, but not exclusively, to assembly of medical instruments.

BACKGROUND

Medical instruments, for example, but not limited to, catheters, probes, and other instruments such as ENT tools, may include miniature cameras for capturing images within the body of a living subject. In order to provide useful data, the image capture equipment often needs to be calibrated after the medical instrument has been assembled prior to initial use.

US Patent Publication 2013/0281821 of Liu, et al., describes a surgical navigation system employs an endoscope and an imaging unit. The endoscope includes an electromagnetic tracker within a working channel of the endoscope for generating electromagnetic sensing signals indicative of one or more poses of the endoscope within an anatomical region, and an endoscopic camera within an imaging channel of the endoscope for generating endoscopic images of the anatomical region. The imaging unit executes an intraoperative calibration of the electromagnetic tracker and the endoscopic camera as a function of an image registration between the preoperative scan image of a calibration site within the anatomical region and one or more endoscopic images of the calibration site within the anatomical region.

U.S. Pat. No. 9,188,973 of Tenney, et al., describes systems and methods that determine a mapping between a first camera system's coordinate system and a second camera system's coordinate system; or determine a transformation between a robot's coordinate system and a camera system's coordinate system, and/or locate, in a robot's coordinate system, a tool extending from an arm of the robot based on the tool location in the camera's coordinate system. The disclosed systems and methods may use transformations derived from coordinates of features found in one or more images. The transformations may be used to interrelate various coordinate systems, facilitating calibration of camera systems, including in robotic systems, such as an image-guided robotic system for hair harvesting and/or implantation.

SUMMARY

There is provided in accordance with an embodiment of the present disclosure, a calibration apparatus including a jig body, a camera, an elongated strip which is deflectable and resilient, a lower groove which is disposed in the jig body, and is configured to receive and grasp the camera therein, an upper groove, which is disposed in the jig body above the lower groove, and is configured to receive and grasp the elongated strip therein so as to position the elongated strip above, and in a fixed relation to, the camera, the upper groove being wider than the lower groove, and an alignment element, which is disposed in the jig body, and is configured to align an end of the camera with an end of the elongated strip.

Further in accordance with an embodiment of the present disclosure the lower groove has a width in the range of 0.5 mm to 2 mm and a height in the range of 0.5 mm to 2 mm, and the upper groove has a width in the range of 1 mm to 6 mm.

Still further in accordance with an embodiment of the present disclosure the lower groove includes a first section having a first width and a second section having a second width wider than the first width, the first section being configured to receive and grasp the camera therein, the second section being configured to receive connections and wires extending from the camera, the first width being in the range of 0.5 mm to 2 mm.

Additionally, in accordance with an embodiment of the present disclosure the alignment element includes an alignment post which is disposed in the lower groove and extends at least up in to the upper groove.

Moreover, in accordance with an embodiment of the present disclosure the upper groove is disposed centrally above the lower groove.

Further in accordance with an embodiment of the present disclosure the upper groove has a height in the range of 0.05 mm to 0.15 mm.

Still further in accordance with an embodiment of the present disclosure the jig body includes at least one side groove extending from the lower groove to exit at a side of the jig body, and configured to receive therein wires extending from the camera.

Additionally, in accordance with an embodiment of the present disclosure a surface of the lower groove and the upper groove includes polytetrafluoroethylene (PTFE) or Polyoxymethylene (POM).

Moreover, in accordance with an embodiment of the present disclosure the elongated strip includes Nitinol.

There is also provided in accordance with another embodiment of the present disclosure, a medical instrument assembly method including disposing a camera in a lower groove of a jig body with an end of the camera abutting an alignment element of the jig body so that the lower groove grasps the camera therein, disposing an elongated strip, which is deflectable and resilient, in an upper groove of the jig body with an end of the elongated strip abutting the alignment element so that the upper groove grasps the elongated strip above, in a fixed relation to, the camera, the upper groove being wider than the lower groove, applying adhesive between the camera and the elongated strip to mechanically connect the camera with the elongated strip, removing the connected camera and elongated strip from the jig body, and disposing the connected camera and elongated strip in a medical instrument.

Further in accordance with an embodiment of the present disclosure the lower groove has a width in the range of 0.5 mm to 2 mm and a height in the range of 0.5 mm to 2 mm, and the upper groove has a width in the range of 1 mm to 6 mm.

Still further in accordance with an embodiment of the present disclosure the elongated strip includes holes, wherein the applying is performed by applying the adhesive through the holes.

Additionally, in accordance with an embodiment of the present disclosure, the method includes disposing wires extending from the camera in at least one side groove of the jig body extending from the lower groove to exit at a side of the jig body.

Moreover, in accordance with an embodiment of the present disclosure the elongated strip includes Nitinol.

Further in accordance with an embodiment of the present disclosure, the method includes disposing light emitting diodes in the medical instrument.

Still further in accordance with an embodiment of the present disclosure, the method includes disposing at least one irrigation tube in the medical instrument.

Additionally in accordance with an embodiment of the present disclosure the lower groove includes a first section having a first width and a second section having a second width wider than the first width, the first section being configured to receive and grasp the camera therein, the second section being configured to receive connections and wires extending from the camera, the first width being in the range of 0.5 mm to 2 mm.

Moreover, in accordance with an embodiment of the present disclosure the alignment element includes an alignment post which is disposed in the lower groove and extends at least up in to the upper groove.

Further in accordance with an embodiment of the present disclosure the upper groove is disposed centrally above the lower groove.

Still further in accordance with an embodiment of the present disclosure the upper groove has a height in the range of 0.05 mm to 0.15 mm.

Additionally, in accordance with an embodiment of the present disclosure a surface of the lower groove and the upper groove includes polytetrafluoroethylene (PTFE) or Polyoxymethylene (POM).

BRIEF DESCRIPTION OF THE DRAWINGS

The present invention will be understood from the following detailed description, taken in conjunction with the drawings in which.

DESCRIPTION OF EXAMPLE EMBODIMENTS

Overview

Figure 1:
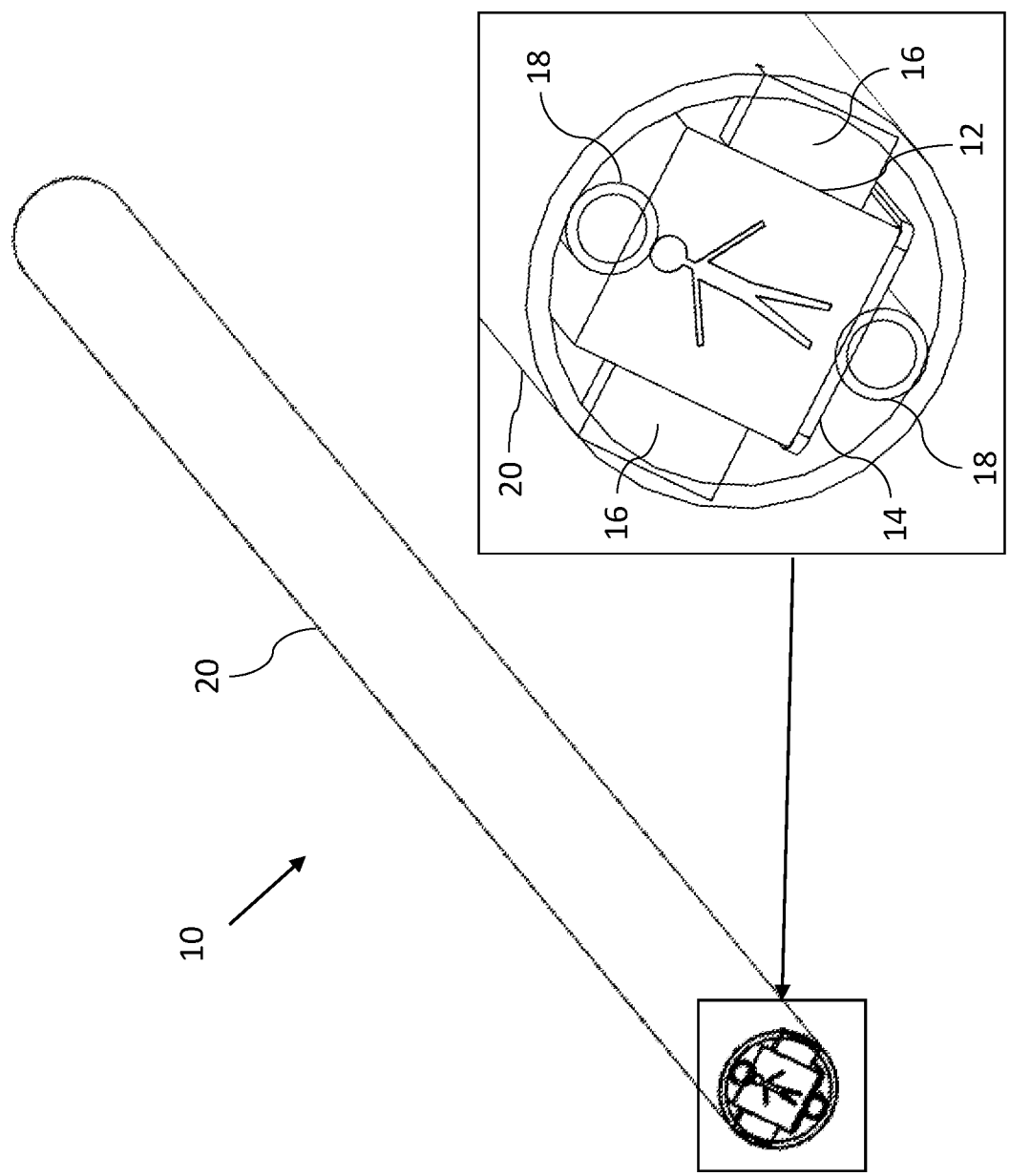
FIG. 1 is a schematic view of a medical instrument constructed and operative in accordance with an embodiment of the present invention.

As mentioned previously, medical instruments, for example, but not limited to, catheters, probes, and other medical instruments such as ENT tools, may include miniature cameras for capturing images within the body of a living subject. In order to provide useful data, the image capture equipment often needs to be calibrated after the medical instrument has been assembled and prior to initial use. The calibration process may be both time consuming and expensive. In some cases, performing calibration after assembly may be very difficult or even impossible.

Embodiments of the present invention, provide a method to efficiently and accurately assemble (and with a reduced cost relative to methods that are known in the art) a medical instrument having a camera using a calibration apparatus including a jig body. The method allows a camera to be mechanically connected to a generally deflectable and resilient elongated strip in a predefined orientation and relative position to within a given accuracy so that a frame captured by the camera is substantially the same (within set calibration limits) as a frame captured by other, cameras and strips connected by the same method and calibration apparatus. Once one of the camera-strip combinations is calibrated, subsequent camera-strip combinations generally do not require further calibration or require less calibration. The elongated strip provides a base to the camera and other proximal components of the medical instrument described in more detail below. The elongated strip with the camera (and optionally other components) is disposed in a guidewire. The positioning of the elongated strip in the guidewire determines the direction in which the medical instrument may be deflected.

The jig body includes various grooves for inserting a camera, the camera wires, and an elongated strip therein. In some embodiments, the grooves are sized and arranged so that the resulting connection between the camera and the elongated strip is accurate to about 0.1% or 1 micron of the desired connection orientation and position. In other embodiments, the accuracy may be more or less, for example, but not limited to, 1% or 10 microns.

A lower groove in the jig body receives and grasps the camera therein. The lower groove includes a first section and a second section which is wider than the first section. It is the first section which receives and grasps the camera therein. The second section receives connections and wires extending from the camera. In some embodiments, the width of the first section may be in the range of 0.5 mm to 2 mm, according to the dimensions of the camera that the first section is intended to grasp. In some embodiments, the lower groove has a height in the range of 0.5 mm to 2 mm, according to the dimensions of the camera to be disposed therein. The width and height dimensions are not limited to the above exemplary values, but may be any suitable value.

The jig body includes at least one side groove extending from the lower groove to exit at a side (or sides) of the jig body. The side grooves may be curved or straight and receive therein the wires extending from the camera.

An upper groove is disposed in the jig body above the lower groove and typically continues to the end of the jig body. The upper groove receives and grasps the elongated strip therein so as to position the elongated strip above, and in a fixed relation to, the camera. The upper groove is wider than the lower groove, reflecting the fact that the elongated strip is generally wider than the camera. The upper groove may have any suitable width according to the width of the elongated strip, but in one embodiment the upper groove has a width in the range of 1 mm to 6 mm. The upper groove may have any suitable height equal to or greater than a thickness of the elongated strip. In some embodiments, the upper groove has a height in the range of 0.05 mm to 0.15 mm. In some embodiments, the upper groove is disposed centrally above the lower groove. However, in other embodiments, the upper groove may be disposed in an off-center alignment according to the desired connection orientation and position of the camera with respect to the elongated strip. As mentioned above the elongated strip is deflectable and resilient and may comprise Nitinol.

The jig body includes an alignment element, which is disposed in the jig body, and is used to align an end of the camera with an end of the elongated strip. In some embodiments, the alignment element comprises an alignment post which is disposed in the lower groove and extends at least up in to the upper groove.

Once the camera and elongated strip are suitably disposed in the jig body, adhesive is applied to mechanically connect the camera with the elongated strip. To prevent the camera and/or elongated strip becoming stuck with adhesive to the jig body, the surface of the lower groove, the upper groove, and possibly other parts of the jig body include a non-stick surface such as polytetrafluoroethylene (PTFE) or Polyoxymethylene (POM). In some embodiments, the jig body is wholly formed of a non-stick material such as PTFE or POM.

The method to assemble the medical instrument includes disposing the camera in the lower groove of the jig body with an end of the camera abutting the alignment element of the jig body so that the lower groove grasps the camera therein and disposing wires extending from the camera in the side groove(s) of the jig body. The method also includes disposing the elongated strip in the upper groove of the jig body with an end of the elongated strip abutting the alignment element so that the upper groove grasps the elongated strip above, in a fixed relation to, the camera. The method also includes applying adhesive between the camera and the elongated strip to mechanically connect the camera with the elongated strip. In some embodiment, the elongated strip comprises holes, and the adhesive is applied through the holes. Once the adhesive has had time to sufficiently mechanically connect the elongated strip with the camera, the method then includes removing the connected camera and elongated strip from the jig body and disposing the connected camera and elongated strip in a medical instrument. In some embodiments light emitting diodes and/or at least one irrigation tube is disposed in the medical instrument.

System Description

Reference is now made to FIG. 1, which is a schematic view of a medical instrument 10 constructed and operative in accordance with an embodiment of the present invention. The medical instrument 10 may include a guidewire 20, for example but not limited to, a compressed coil, holding therein, a camera 12 mounted on an elongated strip 14 (only the end of the elongated strip 14 is visible in FIG. 1), one or more light emitting diodes 16, and one or more irrigation tubes 18. In some embodiments, the guidewire 20 may be disposed within a suitable sheath (not shown). In some embodiments, the medical instrument 10 may omit the light emitting diodes 16 and/or the irrigation tubes 18. In other embodiments, the camera 12 and the elongated strip 14 and optionally the light emitting diodes 16 and/or the irrigation tubes 18 may be disposed in any suitable medical instrument which may, or may not, include the guidewire 20. The medical instrument may be a medical probe, or a catheter or any suitable medical instrument such as an ENT tool, by way of example only. The elongated strip 14 provides a base to the camera 12 and other proximal components (e.g., the light emitting diodes 16 and the irrigation tubes 18) of the medical instrument 10. The positioning of the elongated strip 14 in the guidewire 20 determines the direction in which the medical instrument 10 may be deflected.

Figure 2:
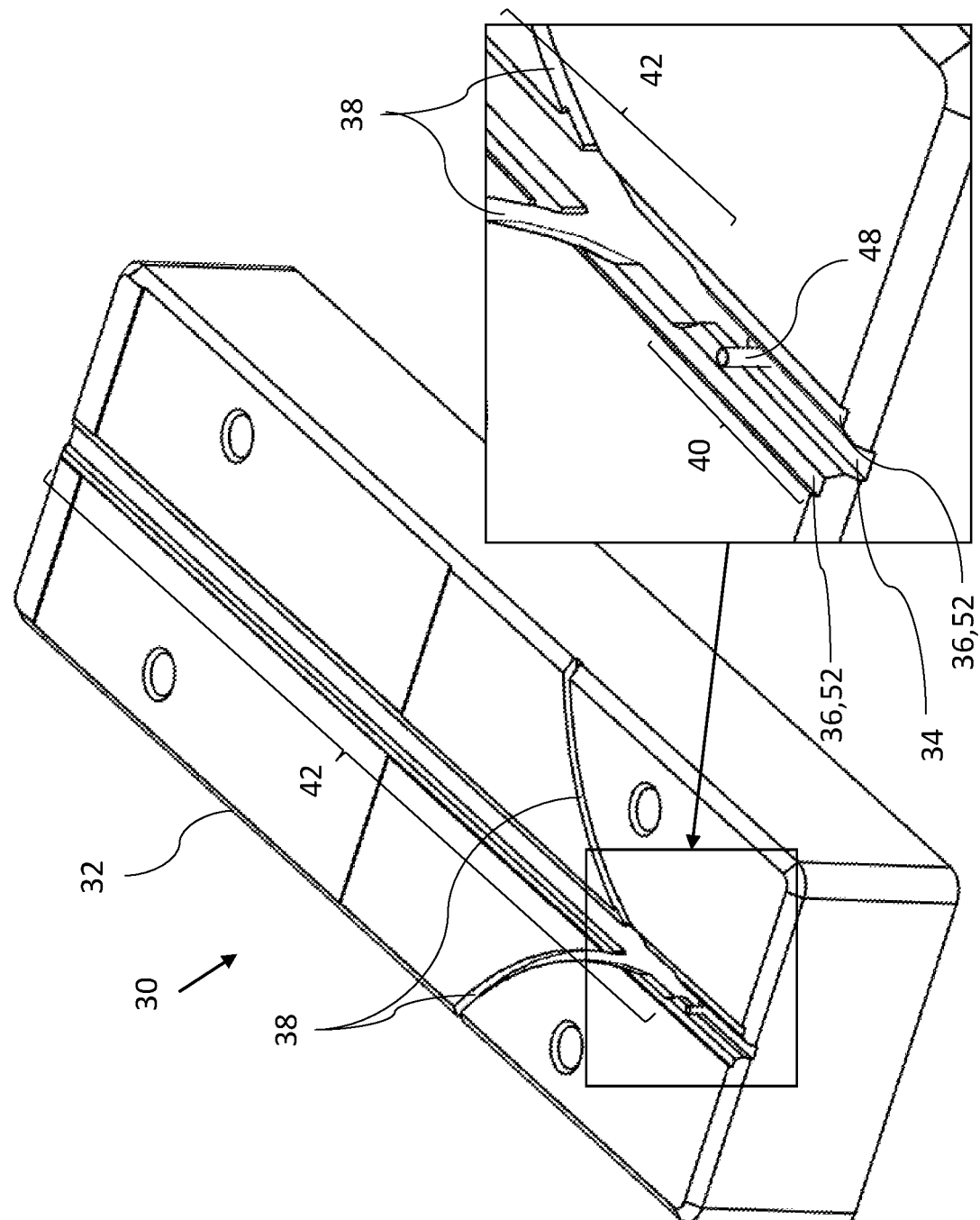
FIG. 2 is a schematic view of a calibration apparatus constructed and operative in accordance with an embodiment of the present invention.
Figure 3:
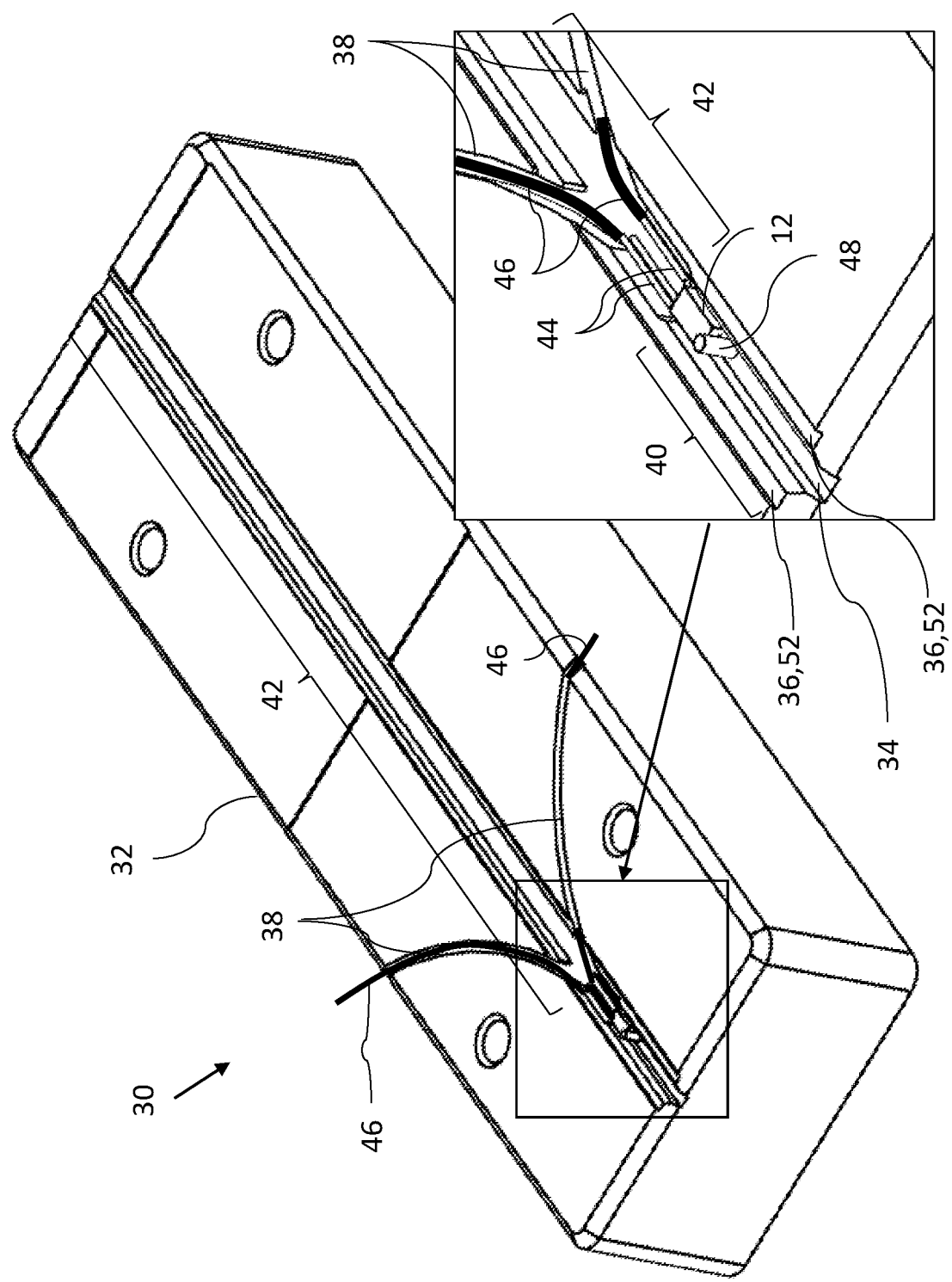
FIG. 3 is a schematic view of the calibration apparatus of FIG. 2 with a camera disposed therein.
Figure 4:
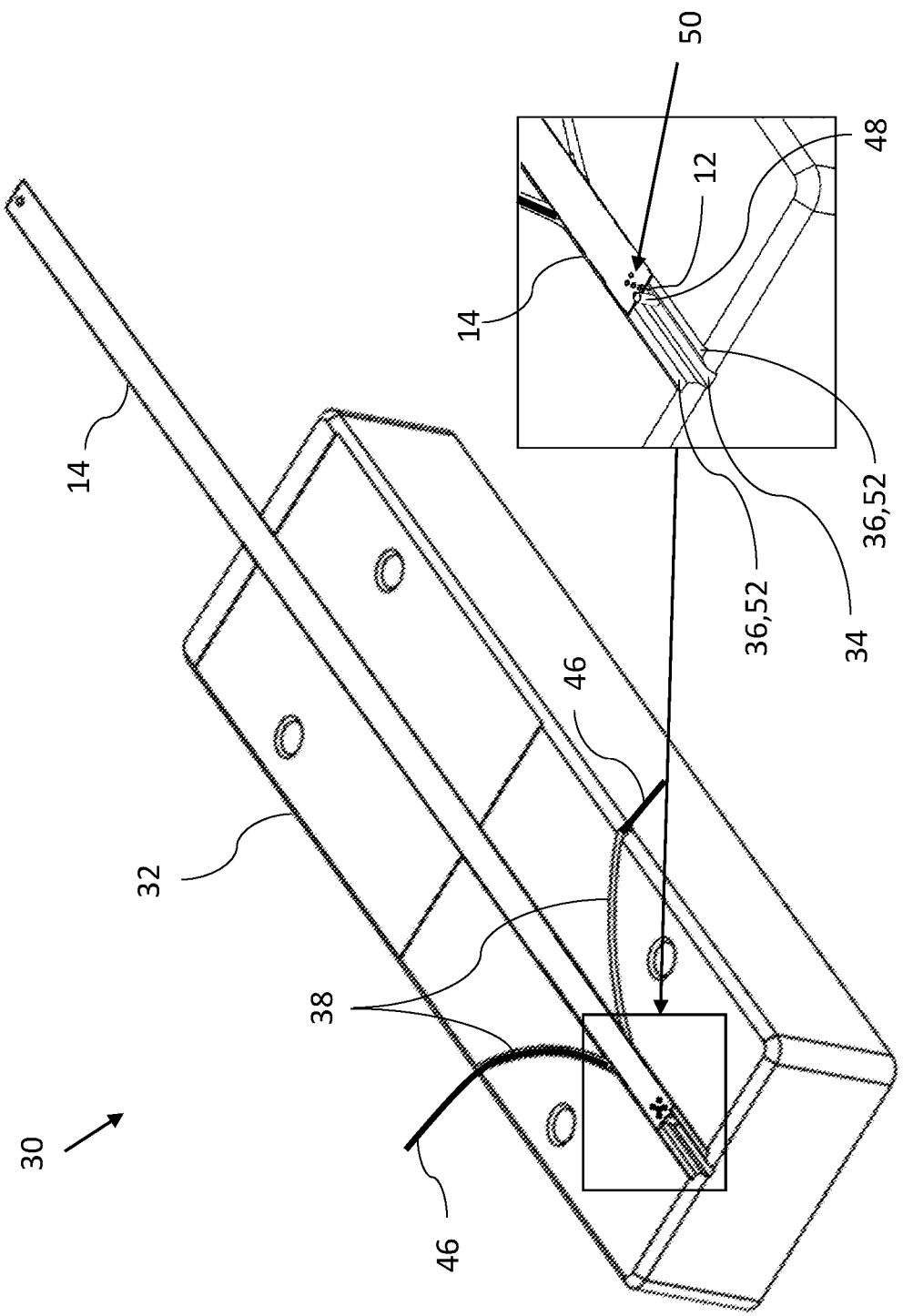
FIG. 4 is a schematic view of the calibration apparatus of FIG. 3 with an elongated strip disposed on top of the camera.

Reference is now made to FIGS. 2-4. FIG. 2 is a schematic view of a calibration apparatus 30 constructed and operative in accordance with an embodiment of the present invention. FIG. 3 is a schematic view of the calibration apparatus 30 of FIG. 2 with the camera 12 disposed therein. FIG. 4 is a schematic view of the calibration apparatus 30 of FIG. 3 with the elongated strip 14 disposed on top of the camera 12.

The calibration apparatus 30 includes a jig body 32, a lower groove 34, an upper groove 36, and two side grooves 38 disposed in the jig body 32. In some embodiments, the lower groove 34 and the upper groove 36 follow a straight path from one end of the jig body 32 to the other.

The lower groove 34 includes a first section 40 and a second section 42. The width of the second section 42 is wider than the width of the first section 40. The first section 40 is configured to receive and grasp the camera 12 therein, as shown in FIG. 3. The second section is configured to receive connections 44 (only some labeled for the sake of simplicity) and wires 46 extending from the camera 12 also shown in FIG. 3. The width and height of the first section 40 is sized to receive and grasp the camera 12 therein in order to ensure that the accuracy of the positioning between the camera 12 and the elongated strip 14 is within the calibration requirements. In some embodiments, the gap between the width of the camera 12 and the width of the first section 40 is in the order of microns. In some embodiments the first section 40 of the lower groove 34 has a width in the range of 0.5 mm to 2 mm, e.g., 1 mm. The width of the first section 40 of the lower groove 34 may be any suitable width according to the size of the camera 12 and the calibration requirements. In some embodiments, the height of the lower groove 34 may be in the range of 0.5 mm to 2 mm, e.g., 1 mm. The height (depth) of the lower groove 34 may be any suitable height according to the size of the camera 12 and the calibration requirements.

The side grooves 38 extend away from the lower groove 34 to exit at either side of the jig body 32. The side grooves 38 are configured to receive therein the wires 46 extending from the camera 12 as shown in FIG. 3. The side grooves 38 help keep the wires 46 away from the elongated strip 14 and prevent the wires 46 from applying upward pressure on the elongated strip 14 which may interfere with the correct position between the camera 12 and the elongated strip 14. Additionally, placing the wires 46 in the side grooves 38 helps stabilize the camera 12 in the first section 40 of the lower groove 34 and prevents forward or backward movement of the camera 12 in the lower groove 34.

The upper groove 36 is disposed in the jig body 32 above the lower groove 34. The upper groove 36 is configured to receive and grasp the elongated strip 14 therein so as to position the elongated strip 14 above, and in a fixed relation to, the camera 12 as shown in FIG. 4.

The upper groove 36 is generally wider than the lower groove 34. In some embodiments, the upper groove 36 is disposed centrally above the lower groove 34. In other embodiments, the upper groove 36 may be disposed non-centrally above the lower groove 34.

The lower groove 34 and upper groove 36 may be viewed as a single groove having a T-shape cross section and side-ledges 52 for resting the elongated strip 14 thereon.

In some embodiments, the upper groove 36 has a width in the range of 1 mm to 6 mm, e.g., 3 mm according to the width of the elongated strip 14. In other embodiments, the upper groove 36 may have any suitable width according to the width of the elongated strip 14 and the calibration requirements.

In some embodiments, the upper groove 36 has a height (depth) in the range of 0.05 mm to 0.15 mm, e.g., 0.08 mm. The height of the upper groove 36 may be set according to a thickness of the elongated strip 14. In other embodiments, the height of the upper groove 36 is not set according to the thickness of the elongated strip 14.

The elongated strip 14 may be longer than the jig body 32. In such a case, the upper groove 36 extends to at least one end of the jig body 32 to allow the elongated strip 14 to extend away from the jig body 32.

The calibration apparatus 30 also includes an alignment element 48, which is disposed in the jig body 32, and is configured to align an end of the camera 12 with an end of the elongated strip 14. In some embodiments, the alignment element 48 comprises an alignment post which is disposed in the lower groove 34 and extends at least up in to the upper groove 36.

As will be described in more detail with reference to FIG. 5, the camera 12 and the elongated strip 14 are mechanically connected together using an adhesive. To prevent the camera 12 and/or the elongated strip 14 from becoming stuck with the adhesive to the jig body 32, a surface of the lower groove 34 and the upper groove 36 may include a non-stick material such as polytetrafluoroethylene (PTFE) or Polyoxymethylene (POM) or any other suitable non-stick material. In some embodiments, the jig body 32 is wholly formed from a non-stick material such as PTFE or POM. The jig body 32 may be any suitable size.

In some embodiments, the elongated strip 14 includes holes 50 therein through which to insert the adhesive. The elongated strip 14 may comprise any suitable materials such that the elongated strip 14 is deflectable and resilient. In some embodiments, the elongated strip 14 is wholly formed from, or partially includes, Nitinol.

Figure 5:
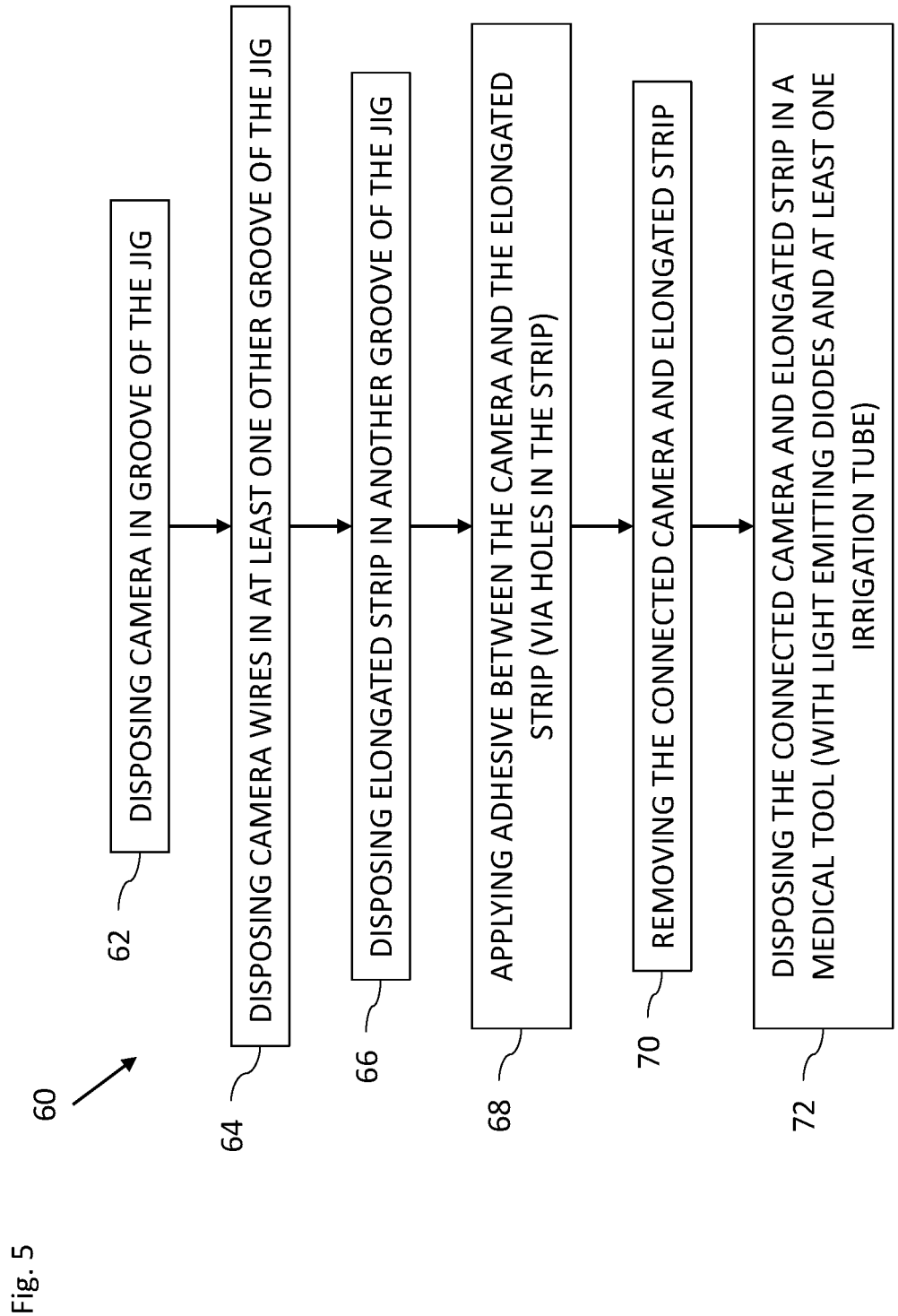
FIG. 5 is a flowchart including exemplary steps in a method of assembling the medical instrument of FIG. 1.

Reference is now made to FIG. 5, which is a flowchart 60 including exemplary steps in a method of assembling the medical instrument 10 of FIG. 1. Reference is also made to FIGS. 1-5. The method of assembling the medical instrument 10 may include the following steps. Some of the steps may be performed in a different order than stated below.

The method includes disposing (block 62) the camera 12 in the lower groove 34 of the jig body 32 with an end of the camera 12 abutting the alignment element 48 of the jig body 32 so that the lower groove 34 grasps the camera 12 therein.

The method also includes disposing (block 64) camera wires 46 extending from the camera 12 in the side groove(s) 38 of the jig body 32 extending from the lower groove 34 to exit at a side of the jig body 32.

The method also includes disposing (block 66) the elongated strip 14, which is deflectable and resilient, in the upper groove 36 of the jig body 32 with an end of the elongated strip 14 abutting the alignment element 48 so that the upper groove 36 grasps the elongated strip 14 above, in a fixed relation to, the camera 12.

The method also includes applying (block 68) adhesive between the camera 12 and the elongated strip 14 to mechanically connect the camera 12 with the elongated strip 14. In some embodiments, the elongated strip 14 comprises holes 50, and the adhesive is applied through the holes 50.

The method also includes removing (block 70) the connected camera 12 and elongated strip 14 from the jig body 32 and disposing (block 72) the connected camera 12 and elongated strip 14, and optionally the light emitting diodes 16 and/or the irrigation tubes 18, in the medical instrument 10.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and subcombinations of the various features described hereinabove, as well as variations and modifications thereof which would occur to persons skilled in the art upon reading the foregoing description and which are not disclosed in the prior art.

What is claimed is:

1. A calibration apparatus, comprising:
   a jig body;
   a camera;
   an elongated strip which is deflectable and resilient;
   a lower groove which is disposed in the jig body, and is configured to receive and grasp the camera therein;
   an upper groove, which is disposed in the jig body above the lower groove, and is configured to receive and grasp the elongated strip therein so as to position the elongated strip above, and in a fixed relation to, the camera, the upper groove being wider than the lower groove; and
   an alignment element, which is disposed in the jig body, and is configured to align an end of the camera with an end of the elongated strip.

2. The apparatus according to claim 1, wherein: the lower groove has a width in the range of 0.5 mm to 2 mm and a height in the range of 0.5 mm to 2 mm; and the upper groove has a width in the range of 1 mm to 6 mm.

3. The apparatus according to claim 1, wherein the lower groove includes a first section having a first width and a second section having a second width wider than the first width, the first section being configured to receive and grasp the camera therein, the second section being configured to receive connections and wires extending from the camera, the first width being in the range of 0.5 mm to 2 mm.

4. The apparatus according to claim 1, wherein the alignment element comprises an alignment post which is disposed in the lower groove and extends at least up in to the upper groove.

5. The apparatus according to claim 1, wherein the upper groove is disposed centrally above the lower groove.

6. The apparatus according to claim 1, wherein the upper groove has a height in the range of 0.05 mm to 0.15 mm.

7. The apparatus according to claim 1, wherein the jig body includes at least one side groove extending from the lower groove to exit at a side of the jig body, and configured to receive therein wires extending from the camera.

8. The apparatus according to claim 1, wherein a surface of the lower groove and the upper groove includes polytetrafluoroethylene (PTFE) or Polyoxymethylene (POM).

9. The apparatus according to claim 1, wherein the elongated strip comprises Nitinol.

* * * * *